United States Patent [19]

Ponsold et al.

[11] 4,231,946
[45] Nov. 4, 1980

[54] 14,15-METHYLENE DERIVATIVES OF THE ESTRANE SERIES AND METHODS FOR PREPARING SAME

[75] Inventors: Kurt Ponsold, Jena; Richard Prousa, Jena-Neulobeda; Michael Oettel, Jena; Joachim Strecke, Jena-Neulobeda; Herbert Hoffmann, Jena, all of German Democratic Rep.

[73] Assignee: VEB Jenapharm, Jena, German Democratic Rep.

[21] Appl. No.: 50,998

[22] Filed: Jun. 22, 1979

[30] Foreign Application Priority Data

Jun. 28, 1978 [DD] German Democratic Rep. ... 206323

[51] Int. Cl.³ .................. C07J 1/00; A61K 31/56
[52] U.S. Cl. .................. 260/397.4; 260/397.5; 424/243
[58] Field of Search .................. 260/397.5, 397.4

[56] References Cited

U.S. PATENT DOCUMENTS

| | | | |
|---|---|---|---|
| 3,232,963 | 2/1966 | Georgian | 260/397.5 |
| 3,300,484 | 1/1967 | Pappo | 260/397.5 |
| 3,318,927 | 5/1967 | Anner et al. | 260/397.5 |

*Primary Examiner*—Elbert L. Roberts
*Attorney, Agent, or Firm*—Michael J. Striker

[57] ABSTRACT

Compounds of the general formula

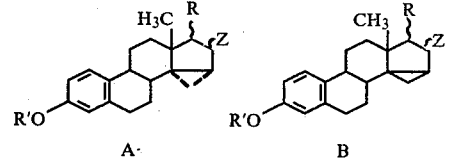

in which R' is hydrogen or a methyl radical;
R is a hydroxyl, acetoxy, arylaminocarbonyloxy, alkylaminocarbonyloxy radical;
Z is hydrogen or a lower alkyl, or
R and Z together are oxygen.

These compounds exhibit a very favorable separation of desirable contraceptive and undesirable uterine and antigonadotrophic properties.

12 Claims, No Drawings

14,15-METHYLENE DERIVATIVES OF THE ESTRANE SERIES AND METHODS FOR PREPARING SAME

BACKGROUND OF THE INVENTION

The invention concerns 14α,15α- and 14β,15β-methylene derivatives of the estrane series, which have the following general formulae in which R' is hydrogen or a methyl radical;
R is a hydroxyl, acetoxy, arylaminocarbonyloxy, alkylaminocarbonyloxy radical;
Z is hydrogen or a lower alkyl, or
R and Z together are oxygen, and which because of their hormonal and antihormonal properties are of therapeutic importance, 3-methoxy-14α,15α- and 14β,15β-methylene-estra-1,3,5(10)-triene-17α- and 17β-ols as well as 3-methoxy-17α-methyl-14β-15β-methylene-estra-1,3,5(10)-triene-17β-ol exhibiting strong antifertility effects which particularly in the case of 3-methoxy-14α-15α-methylene-estra-1,3,5(10)-triene-17α-ol and 3-methoxy-14β,15β-methylene-estra-1,3,5(10)-triene-17α- and 17β-ol as well as in the case of 3-methoxy-17α-methyl-14β-15β-methylene estra-1,3,5(10)-triene-17β-ol are associated with a very favorable separation of desirable contraceptive and undesirable uterine and antigonadotrophic activities.

It is known that olefins may be methylenated by the Simmons-Smith reaction with dihalogen methanes and a zinc-copper pair or with diazomethane and zinc iodide. Also, steroid olefins were methylenated with dihalogen methanes and zinc copper. Under unfavorable steric conditions methylene addition, however, may be rendered more difficult or may be even suppressed in the case of homoallyl alcohols such as 3-hydroxy-Δ5(6)-steroids. Methylene addition to the Δ14-double bond has not yet been described.

SUMMARY OF THE INVENTION

It is principal object of the present invention to produce 14α,15α-methylene and 14β,15β-methylene derivatives of the estrane series of the foregoing general formulae so as to make use of their favorable biological properties.

It is a further object of this invention to provide a technologically realizable process for producing 14α,15α- and 14β,15β-methylene derivatives of the estrane series having the foregoing general formulae.

According to the invention 14,15-methylene derivatives of the estrane series having the general formulae where R' is hydrogen or a methyl radical;
R is a hydroxyl, acetoxy, arylaminocarbonyloxy, alkylaminocarbonyloxy radical;
Z is hydrogen or a lower alkyl;
R and Z together are oxygen are produced by converting the Δ14,17α- or 17β-hydroxy compounds of the estrane series, which can include lower alkyls in the 17 position, if required, with dihalogen methanes and a zinc-copper pair or with diazomethane and zinc iodide, respectively, in suitable organic solvents, preferably ethers, at room temperature up to 50° C. so as to obtain the 14α,15α-methylene-17α-hydroxy or 14β,15β-methylene-17β-hydroxy compounds of the estrane series and oxidizing the secondary 14,15-methylene-17-alcohols to 17-ketones in each case by means of chromic oxide and aqueous sulphuric acid in acetone, reducing the resulting 14α-15α- and 14β-15β-methylene-17-ketones of the estrane series with complex metal hydrides so as to obtain 14α-15α-methylene-17α-ols and 14β-15β-methylene-17β-ols, respectively, as well as the isomeric compounds, namely the 14α-15α-methylene-17β-ols and 14β-15β-methylene-17α-ols, respectively, subsequently separating these mixtures by chromatography and, if required, acetylating the secondary 14,15-methylene-17-ols of the estrane series in the 17 position in accordance with conventional procedures and converting them to the alkyl- or arylaminocarbonyloxy compounds.

The single reaction steps of the process are further illustrated by the partial formula pattern, which follows.

Formula pattern

Z = H, lower alkyl

Z = H, lower alkyl
R = H, Ac, CONHR₁
R₁ = alkyl, aryl

Z = H
R = H, Ac, CONHR₁
R₁ = alkyl, aryl

Z = H
R = H, Ac, CONHR₁
R₁ = alkyl, aryl

The process is performed advantageously as follows:

The Δ14-17β-hydroxy compounds of the estrane series which serve as starting materials for the process are part of the prior art. Methylene iodide and methylene bromide are suitable for the reaction; suitable solvents are especially ether and ethereal mixtures—preferably diethyl ether and mixtures of diethyl ether and ethylene glycol dimethyl ether—but also hydrocarbons, cyclic hydrocarbons and halogenated hydrocarbons as well as their mixtures with ethers.

For the conversion with methylene iodide in diethyl ether—ethylene glycol dimethyl ether the zinc-copper pair prepared from zinc dust and aqueous cupric sulphate solution according to S. Shank and H. Schechter (J. Org. Chem. 24 (1959), 1825) is sufficiently active; for the conversion in diethyl ether alone and in most of the other solvents mentioned, as well as for the conversion with methylene bromide in all the solvents mentioned the more active zinc-copper pair as is prepared from zinc and cupric acetate in glacial acetic acid according to S. LeGoff (J. Org. Chem. 29 (1964), 2049) is preferred.

The reaction can be performed at room temperature; however, preferable are temperatures ranging between 30° and 50° C. For oxidizing the secondary 17$\alpha$- and 17$\beta$-hydroxy-14,15-methylene compounds, a mixture of chromic oxide and aqueous sulphuric acid in acetone is used; the reduction of the resulting ketones is performed with sodium borohydride in methanol or with lithium aluminum hydride, lithium trimethoxyaluminum hydride or lithium tri-(tert-butoxy) aluminum hydride in tetrahydrofuran. When sodium boro-hydride is used in the reduction of the 14$\alpha$-15$\alpha$-methylene-17-ketones of the estrane series the ratio of the resulting 14$\alpha$-15$\alpha$-methylene-17$\alpha$- and 17$\beta$-ols will be 1:1.3; the ratio for lithium aluminum hydride will be 2.3:1. In the case of reducing the 14$\beta$-15$\beta$-methylene-17-ketones of the estrane series by means of sodium borohydride the 14$\beta$,15$\beta$-methylene-17$\alpha$- and 17$\beta$-ols are resulting in the ratio of 1.5:1; when lithium aluminum hydride is used, the ratio will be 1:1.

In a variant of the process, the conversion of the above-mentioned 14,15-unsaturated 17-alcohols to the corresponding 14,15-methylene compounds is not performed with methylene iodide or methylene bromide and zinc-copper as indicated above, but with diazomethane and zinc iodide in ether.

In this case, the ethereal solution of the 14,15-unsaturated 17-hydroxy steroids optionally substituted by alkyl in the 17 position, if desired, is added at a temperature of 0° C. to the suspension of zinc iodide in an ethereal solution of diazomethane.

The secondary 14,15-methylene-17-ols are acetylated in the 17 position with acetic anhydride-pyridine or converted with isocyanates directly or in suitable solvents such as benzene to yield the corresponding alkyl and arylamino-carbonyloxy derivatives, respectively. The corresponding 14,15-methylene-17-ols of the estrane series having a free 3-hydroxy group are first converted by means of phosgene in benzene solution to the 17-chlorocarbonic acid esters from which by reaction with amines the 17-alkyl and arylaminocarbonyloxy derivatives are formed. Isolation and purification of the compounds obtained according to the process can be effected by conventional methods.

The compounds which can be produced by the processes according to the invention are new; their preparation has not yet been described.

The favorable biological properties of the named compounds of the process according to the invention are to be further illustrated and described in the example of 3-methoxy-14$\beta$-15$\beta$-methylene-estra-1,3,5(10)-triene-17$\beta$-ol (test designation STS 593). The contraceptive activity of this compound in the female rat related to IHE$_1$ is in the range of that of mestranol; the compound has nearly double the activity of ethynylestradiol (Tables 1 and 2).

STS 593 was weaker than ethynylestradiol by a factor of 9 in its estrogenic properties as shown by the Allen-Doisy test in ovariectomized mice. The compound was only 7% as active as the standard mestranol in producing a uterine response in infantile rats (Table 3), whereas the antiestrogenic properties exceeded those of clomiphene citrate by a factor of 1.4.

The compound was four times weaker than mestranol in antigonadotrophic effect in rats (Table 4). The effective dose for the HE$_{50}$ was close to 0.65 mg/kg of body-wt./5 d, while mestranol has the same effect at a dose as low as 0.15 mg/kg of body-wt./5 d.

STS 593 when applied to infantile male rats orally over 6 days at total doses of between 0.75 and 3.0 mg/animal, did not show any androgenic, anabolic, and antiandrogenic effects. It also proved to be lacking in progestagenic activity, but it showed antiprogestanenic properties when applied orally to rabbits at a dosage of 50 mg/kg. The HE of 97.3% is significant (Table 5).

Thus, 3-methoxy-14$\beta$-15$\beta$-methylene-estra-1,3,5(10)-triene-17$\beta$-ol as compared to mestranol shows a more favorable separation of contraceptive properties and undesirable (estrogenic, antigonadotrophic, progestagenic) side-effects. Moreover, the compound produces antiestrogenic and antiprogestagenic effects which are important for its therapeutic use. Besides, it is characterized by a favorable separation of contraceptive activity and undesirable post implantation fetal damage. In this context the compound is better than mestranol by a factor of 6.

Table 6 illustrates the favorable biological properties of the other compounds mentioned above. Among these, 3-methoxy-14$\alpha$,15$\alpha$-methylene-estra-1,3,5(10)-triene-17$\beta$-ol (test designation STS 651, see also Table 2) and 3-methoxy-17$\alpha$-methyl-14$\beta$,15$\beta$-methylene-estra-1,3,5(10)-triene-17$\beta$-ol (test designation STS 681) distinguish themselves by the strongest contraceptive activities related to IHE$_1$, followed by 3-methoxy-14$\alpha$,15$\alpha$-methylene-estra-1,3,5(10)-triene-17$\alpha$-ol (test designation STS 652) and 3-methoxy-14$\beta$-15$\beta$-methylene-estra-1,3,5(10)-triene-17$\alpha$-ol (test designation STS 592) 3-methoxy-14$\alpha$-15$\alpha$-methylene-estra-1,3,5(10)-triene-17$\beta$-ol producing the strongest uterine response (Table 6: Uterine activity represented by the dose required for doubling the uterine weight).

3-methoxy-17$\alpha$-methyl-14$\beta$,15$\beta$-methylene-estra-1,3,5-(10)-triene-17$\beta$-ol, 3-methoxy-14$\alpha$,15$\alpha$-methylene-estra-1,3,5-(10)-triene-17$\alpha$-ol and above all, 3-methoxy-14$\beta$,15$\beta$-methylene-estra-1,3,5(10)-triene-17$\alpha$-ol exhibit distinctly weaker uterine activities. Hence, among the compounds of Table 6 3-methoxy-14$\beta$,15$\beta$-methylene-estra-1,3,5(10)-triene-17$\alpha$-ol exhibits the most favorable separation of the desirable contraceptive and the undesirable estrogenic effects in mice.

3-methoxy-14$\beta$,15$\beta$-methylene-estra-1,3,5(10)-triene-17$\beta$-ol can be used to special advantage as a contraceptive because of its favorable endocrinological activity spectrum. The compound can additionally be used to induce ovulation and to treat hormone-dependent tumors because of its marked antiestrogenic properties.

Gestation and nidation inhibition expressed in % were used as parameters for antifertility effects. GHE$_1$ (gestation inhibitory effect) and IHE$_1$ (nidation inhibitory effect) were related to the inhibition of the total of gestations or nidations, GHE$_2$ and IHE$_2$ were related to the inhibition of normal gestations or nidations within each group. All gestations were referred to as normal if exhibiting at least 1 normal implantation site. $GHE_1$, $GHE_2$, $IHE_1$ and $IHE_2$ were calculated using the following formulae:

$$GHE_1 (\%) = 1 - \frac{x_v \cdot n_k}{n_v \cdot x_k} \cdot 100$$

$$IHE (\%) = 1 - \frac{\bar{f_v}}{\bar{f_k}} \cdot 100$$

n = number of females inseminated in each group
v = test group
k = control group (sesame oil)
x = number of all gestations ($GHE_1$) and of normal gestations ($GHE_2$) p. group, respectively
$\bar{f}$ = average number ($\bar{x}$) of all implantations ($IHE_1$) and of normal implantations ($IHE_2$) p. female inseminated within a group, respectively.

The comparison of the relative incidence of gestations was performed by the Ryan test, the comparison of the number of implantations by the Dunn test.

For $GHE_1$ and $GHE_2$ the ED (effective doses) for the HE (inhibitory effect) 0%, 50%, and 95% as far as possible were determined by means of the probit analysis. The $ED_{50}$ for $IHE_1$ and $IHE_2$ were determined graphically. The results are shown in Tables 1, 2, and 6.

Table 2-continued

Comparison between the contraceptive effects of STS 593 and STS 651 and those of mestranol and ethynylestradiol in the Nidation Inhibition Test

| Substance | ED | ED in mg/kg of body-wt. p.o. for | | | |
|---|---|---|---|---|---|
| | | $GHE_1$ | $GHE_2$ | $IHE_1$ | $IHE_2$ |
| | 95 | 0.583 | 0.265 | | |

+Data from trial No. 2 in Table 1. According to trial No. 1 the $ED_{50}$ for $IHE_1$ and $IHE_2$ was calculated as being 0.175 and 0.155 mg/kg of body-wt. p.o., respectively.

Table 3

Comparison of uterine activity in infantile female Wistar rats produced by STS 593 and mestranol

| Substance | Total dose /uμ/animal over 3 days p.o. | n | Uterine weight $\bar{x}$ mg | $s_{\bar{x}}$ |
|---|---|---|---|---|
| Sesame oil | 0.6 ml | 10 | 31.93 | 2.68 |
| Mestranol | 0.6 | 10 | 70.11+ | 1.59 |
| " | 6.0 | 10 | 95.45+ | 4.81 |
| STS 593 | 0.1 | 10 | 27.63 | 1.29 |
| " | 1.0 | 10 | 52.40+ | 3.66 |
| " | 10.0 | 10 | 75.90+ | 3.40 |

+ = significance $p < 0.05$

Table 1

Antinidation activity of STS 593 as compared to mestranol in inseminated rats when treated on the 1st day of gestation

| Substance | Dose mg/kg p.o. | Female rats inseminated n | pregnant total | Implantations per of n normal | female total | of (x̄) normal | $GHE_1$ % | $GHE_2$ % | $IHE_1$ % | $IHE_2$ % |
|---|---|---|---|---|---|---|---|---|---|---|
| 1ST trial 1975 | | | | | | | | | | |
| sesame oil | 5 ml | 14 | 14 | 14 | 12.5 | 12.5 | | | | |
| mestranol | 0.2 | 12 | 11 | 1+ | 6.8+ | 0.2+ | 8.3 | 91.7 | 45.3 | 98.7 |
| STS 593 | 0.1 | 12 | 10 | 10 | 8.8 | 8.2 | 16.7 | 16.7 | 30.0 | 34.7 |
| " | 0.3 | 12 | 8 | 5+ | 3.8+ | 3.4+ | 33.3 | 58.3 | 70.0 | 72.7 |
| " | 0.9 | 12 | 6+ | 3+ | 1.7+ | 0.7+ | 50.0 | 75.0 | 86.7 | 94.7 |
| 2nd trial 1978 | | | | | | | | | | |
| sesame oil | 5 ml | 12 | 12 | 12 | 13.0 | 13.0 | | | | |
| mestranol | 0.2 | 10 | 6 | 0+ | 3.8 | 0+ | 40 | 100 | 70.8 | 100 |
| STS 593 | 0.08 | 10 | 9 | 9 | 10.6 | 10.5 | 10 | 10 | 18.5 | 19.2 |
| " | 0.16 | 10 | 10 | 2+ | 8.8+ | 2.3+ | 0 | 80 | 32.3 | 82.3 |
| " | 0.32 | 10 | 5+ | 3+ | 3.3+ | 1.8+ | 50 | 70 | 74.6 | 86.1 |
| " | 0.64 | 10 | 4+ | 0+ | 1.6+ | 0+ | 60 | 100 | 87.7 | 100 |
| " | 1.28 | 10 | 2+ | 0+ | 1.5+ | 0+ | 80 | 100 | 88.5 | 100 |

+ = significance data $p < 0.05$

Table 2

Comparison between the contraceptive effects of STS 593 and STS 651 and those of mestranol and ethynylestradiol in the Nidation Inhibition Test

| Substance | ED | ED in mg/kg of body-wt. p.o. for | | | |
|---|---|---|---|---|---|
| | | $GHE_1$ | $GHE_2$ | $IHE_1$ | $IHE_2$ |
| Mestranol | 05 | 0.097 | 0.065 | | |
| | 50 | 0.340 | 0.163 | 0.17 | 0.15 |
| | 95 | 1.107 | 0.387 | | |
| Ethynyl-estradiol | 50 | ≦0.45 | <0.30 | 0.37 | <0.21 |
| STS 593+ | 05 | 0.078 | 0.044 | | |
| | 50 | 0.474 | 0.147 | 0.22 | 0.112 |
| | 95 | 2.591 | 0.454 | | |
| STS 651 | 05 | 0.059 | 0.043 | | |
| | 50 | 0.183 | 0.110 | 0.107 | 0.096 |

Table 4

Antigonadotrophic activity of STS 593

| Substance | Total dose mg/kg of body-wt. p.o. | n | Testicular mass $\bar{x} \pm s_{\bar{x}}$ mg | IE % | HE 50 for mg/kg of body-wt. |
|---|---|---|---|---|---|
| Initial control | — | 10 | 159.2 ± 5.4 | | |
| Final control | — | 10 | 346.1 ± 27.1 | | |
| STS 593 | 0.25 | 9 | 312.4 ± 42.5 | 18.1 | |
| " | 0.50 | 10 | 272.3 ± 37.7 | 39.6 | 0.65 |
| " | 1.00 | 10 | 217.6 ± 24.2 | 68.9 | |

Table 5

Progestagenic and antiprogestagenic activities of STS 593 in infantile rabbit uteri as shown by the McPhail test

| Substance | Total dose over 4 days | n | McPhail index $\bar{x}$ | HE % |
|---|---|---|---|---|
| Progesterone | 4 mg/animal/s.c. | 6 | 3.0 | |
| STS 593 | 2 mg/kg/p.o. | 5 | 0 | |

Table 5-continued

Progestagenic and antiprogestagenic activities of STS 593 in infantile rabbit uteri as shown by the McPhail test

| Substance | Total dose over 4 days | n | McPhail index $\bar{x}$ | HE % |
|---|---|---|---|---|
| STS 593 + progesterone | 2 mg/kg/p.o. 4 mg/animal/s.c. | 6 | 3.8 | |
| STS 593 + progesterone | 10 mg/kg/p.o. 4 mg/animal/s.c. | 5 | 2.2 | 26.7 |
| STS 593 + progesterone | 50 mg/kg/p.o. 4 mg/animal/s.c. | 6 | 0.08 | 97.3+ |

+* = significance p<0.05

Table 6

Uterine and contraceptive activities produced by selected 14,15-methylene-17-ol-estratrienes in mice

| STS | Total dose for doubling uterine fresh weight in μg/animal/p.o. | THE, % after single application of 10 mg/kg of body-wt. on the 1st day of gestation p.o. |
|---|---|---|
| 593 | 0.45 | 80.2 |
| 651 | 0.2 | 84.4 |
| 652 | 3.0 | 60.0 |
| 592 | 7.0 | 35.0 |
| 681 | 0.56 | 81.7 |
| 594 | 100 | |
| 595 | 100 | |

Test designation STS 594 17α-phenylaminocarbnoyloxy-14β,15β-methylene-estra-1,3,5(10)-triene-3-methylether
Test designation STS 595 17β-phenylaminocarbonyloxy-14β,15β-methylene-estra-1,3,5(10)-triene-3-methylether

DESCRIPTION OF THE PREFERRED EMBODIMENTS

1. 3-methoxy-14β,15β-methylene-estra-1,3,5(10)-triene-17β-ol (a) 1 g of 3-methoxy-estra-1,3,5(10),14-tetraene-17βol, dissolved in 20 ml of ethylene glycol dimethyl ether and 20 ml of diethyl ether, is mixed with 2 g of zinc-copper pair (prepared according to S. Shank and H. Schechter, J. Org. Chem. 24 (1959), 1825); 2 ml of methylene iodide is added dropwise. The preparation is stirred in the presence of nitrogen or argon first at room temperature and later at a temperature of 40° C. for 4 to 6 hours in total, another 1.5 ml of methylene iodide and 2 g of zinc-copper altogether being added in the course of the reaction. Subsequently the preparation is filtered, diluted with ether or a mixture of ether and benzene, repeatedly washed with saturated aqueous ammonium chloride solution and water and, after drying the organic phase with sodium sulphate and evaporating, the oily residue is mixed with petroleum ether and crystallized.

Yield: 800 mg. (75.2%), flash point: 137° to 138° C. specific optical rotation $[\alpha]_D^{25}+119.5°$ (c=1; CHCl$_3$)

(b) 1.5 g of active zinc-copper complex (prepared according to E. LeGoff, J. Orgn. Chem. 29 (1964), 2049) is dissolved in 40 ml of absolute ether and mixed with 1 ml of methylene bromide. In the presence of nitrogen or argon the preparation is warmed to 40° C. Then 1 g of 3-methoxy-estra-1,3,5(10)-14-tetraene-17β-ol is dissolved in 5 ml of absolute ether and another 1.2 ml of methylene bromide is added to the reaction mixture. The product is stirred for 1.5 hours at 40° C., then diluted with ether and benzene, filtered and, after repeatedly washing the filtrate with saturated aqueous ammonium chloride solution and water, the organic phase is dried with sodium sulphate and evaporated.

The crystalline residue is recrystallized from petroleum ether and methanol.

Yield: 745 mg (70%).

(c) 2.4 g of zinc iodide are suspended in 10 ml of absolute ether. The suspension is cooled down to 0° C., and 30 ml of 0.5 molar ethereal diazomethane solution are added dropwise. The mixture is restricted to half the volume on the rotary evaporator and then mixed with 300 mg of 3-methoxy-estra-1,3,5(10),14-tetraene-17β-ol in 10 ml of ether. After 30 minutes of stirring, during which time the reaction mixture reaches room temperature, and subsequent 4 hours of warming to 40° C., the mixture is filtered, diluted with ether and repeatedly washed with saturated aqueous ammonium chloride solution and water. The oily residue which remains from evaporation is crystallized by treating it with petroleum ether.

Yield: 1.4 g (60%).

2. 3-methoxy-14α-15α-methylene-estra-1,3,5(10)-triene-17α-ol

To a solution of 1 g of 3-methoxy-estra-1,3,5(10),14-tetraene-17α-ol in 25 ml of ethylene glycol dimethyl ether and 25 ml of diethyl ether is added 3 g of zinc-copper pair (according to 1.) and 3 ml of methylene iodide. The preparation is stirred in the presence of nitrogen or argon for 2 to 3 hours first at room temperature and later at 40° C., then filtered, diluted with ether or a mixture of ether and benzene and, after repeated washings with saturated aqueous ammonium chloride solution and water, dried with sodium sulphate and evaporated. The residue is crystallized from petroleum ether.

Yield: 780 mg (73.3%), flash point: 143° to 145° C.; specific optical rotation $[\alpha]_D^{25}+107.8°$ (c=1; CHCl$_3$).

3. 3-methoxy-14β,15β-methylene-estra-1,3,5(10)-triene-17αol 400 mg of 3-methoxy-14β,15β-methylene-estra-1,3,5(10)-triene-17-one dissolved in 300 ml of methanol are mixed with 380 mg of sodium borohydride at 0° C. and set aside overnight at room temperature. Subsequently the mixture is reduced to half its volume in vacuum and poured into cold aqueous acetic acid. The precipitate is dried, and preparative layer chromatography on silica gel (mobile phase: benzene/acetone 3:2) yields 90 mg of 3-methoxy-14β,15β-methylene-estra-1,3,5(10)-triene-17β-ol and 210 mg of 3-methoxy-14β,15β-methylene-estra-1,3,5(10)-triene-17α-ol. Flash point 117° to 119° C., specific optical rotation: $[\alpha]_D^{25}+104.0°$ (c=1; CHCl$_3$).

4. 3-methoxy-14α,15α-methylene-estra-1,3,5(10)-triene-17β-ol (a) 400 mg of 3-methoxy-14α,15α-methylene-estra-1,3,5(10)-triene-17-one dissolved in 150 ml of methanol are mixed with 400 mg of sodium borohydride at 0° C. and set aside overnight at room temperature. The mixture is poured into cold aqueous acetic acid. The precipitate is dried and preparative layer chromatography on silica gel (mobile phase: benzene/acetone/methanol 45:5:1) yields 180 mg of 3-methoxy-14α,15α-methylene-estra-1,3,5(10)-triene-17α-ol and 220 mg of 3-methoxy-14α,15α-methylene-estra-1,3,5(10)-triene-17β-ol.

Flash point: 118° to 120° C., specific optical rotation $[\alpha]_D^{25} +132.0°$ (c=1; CHCl$_3$).

(b) 100 mg of 3-methoxy-14α,15α-methylene-estra-1,3,5-(10)-triene-17-one dissolved in 12 ml of absolute tetrahydrofuran are mixed with 100 mg of lithium aluminum hydride at 0° C. and set aside for 1.5 hours at room temperature. After adding ethyl acetate and ether the product is washed with saturated aqueous ammonium chloride solution and water, and the organic layer is separated, followed by drying with sodium sulphate and evaporating under vacuum. After preparative layer chromatography on silica gel (mobile phase: benzene/acetone/methanol 45:5:1) the residue yields 60 mg of 3-methoxy-14α,15α-methylene-estra-1,3,5(10)-triene-17α-ol and 26 mg of 3-methoxy-14α,15α-methylene-estra-1,3,5(10)-triene-17β-ol.

5.
3-methoxy-17α-methyl-14β,15β-methylene-estra-1,3,5(10)-triene-17β-ol 500 mg of 3-methoxy-17α-methyl-estra-1,3,5(10)-14-tetraene-17β-ol dissolved in 12 ml of ethylene glycol dimethyl ether and 12 ml of diethyl ether are mixed with 1.5 g of zinc-copper pair (according to 1.), and 1.5 ml of methylene iodide is added dropwise thereto. In the presence of nitrogen or argon the preparation is stirred for 2 hours as a whole, first at room temperature and later at 40° C. Subsequently, the preparation is filtered, diluted with ether and benzene, washed repeatedly with saturated ammonium chloride solution and water, and the organic phase is concentrated. The residue is recrystallized from methanol.

Yield: 300 mg (60%), flash point: 158° to 160° C., specific optical rotation $[\alpha]_D^{25} +120.8°$ (c=1; CHCl$_3$).

6.
3-methoxy-14β,15β-methylene-estra-1,3,5(10)-triene-17-one

To a solution of 1 g of 3-methoxy-14β,15β-methylene-estra-1,3,5(10)-triene-17β-ol in 70 ml of acetone is added 2 ml of a solution of 4 g of chromic oxide, 2 ml of concentrated sulphuric acid and 10 ml of water at room temperature. After 20 minutes the preparation is poured into water and the precipitate recovered by filtration, which is washed neutral and after drying recrystallized from methanol.

Yield: 950 mg (95%), flash point: 160° to 162° C., specific optical rotation $[\alpha]_D^{25} +256.7°$ (c=1; CHCl$_3$).

7.
3-methoxy-14α,15α-methylene-estra-1,3,5(10)-triene-17-one

To a solution of 1 g of 3-methoxy-14α,15α-methylene-estra-1,3,5(10)-triene-17α-ol in 70 ml of acetone is added at room temperature 2 ml of a solution of 4 g of chromic oxide, 2 ml of concentrated sulphuric acid and 10 ml of water. After 20 minutes the preparation is poured into water and the precipitate recovered by filtration, which is washed neutral and recrystallized from methanol.

Yield: 930 mg (93%), flash point: 114° to 116° C., specific optical rotation: $[\alpha]_D^{25} +99.2°$ (c=1; CHCl$_3$).

8.
17α-phenylaminocarbonyloxy-14β,15β-methylene-estra-1,3,5(10)-triene-3-methylether 1 g of 3-methoxy-14β,15β-methylene-estra-1,3,5(10)-triene-17β-ol is dissolved in 2 ml of benzene, and 1 ml of phenyl isocyanate is added thereto, both reactions being performed at room temperature. The product is set aside for 2 hours and then heated to 80° C.; subsequently the solvent is removed under vacuum, and the remaining oil is crystallized by mixing with hexane, then washed with hexane and recrystallized from methanol.

Yield: 1.1 g (88%), flash point: 129° to 130° C., specific optical rotation: $[\alpha]_D^{25} +76.80°$ (c=1; CHCl$_3$).

9.
17β-phenylaminocarbonyloxy-14β,15β-methylene-estra-1,3,5(10)-triene-3-methylether 1 g of 3-methoxy-14β,15β-methylene-estra-1,3,5(10)-triene-17β-ol is mixed with 2 ml of phenylisocyanate and heated to 80° C. for 1 hour. After adding hexane thereto, the solution is separated from the crystalline residue that has developed; the latter is rewashed with hexane and recrystallized from methanol.

Yield: 1 g (80%), flask point: 185° to 187° C., specific optical rotation: $[\alpha]_D^{25} +91.4°$ (c=1; CHCl$_3$).

10.
17α-phenylaminocarbonyloxy-14β,15β-methylene-estra-1,3,5(10-triene-3β-ol

To a solution of 500 mg of 14β,15β-methylene-estra-1,3,5(10)-triene-3β,17β-diol in 5 ml of absolute tetrahydrofuran is added 10 ml of an approximately 10% solution of phosgene in benzene, and the product is set aside overnight at room temperature.

The excess phosgene is removed by blowing air therethrough, and the solution is evaporated in vacuum. To the residue (600 mg) is added a solution of 1.2 ml of aniline in 50 ml of acetone, and the product is set aside at room temperature for 2.5 hours. Finally it is poured into aqueous hydrochloric acid, during which process the crude product precipitates, which is recrystallized from wet isopropanol.

Yield: 530 mg (80%), flash point: 209.5° to 211.5° C., specific optical rotation: $[\alpha]_D^{25} +78.8°$ (c=1; CHCl$_3$).

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A compound of the formula

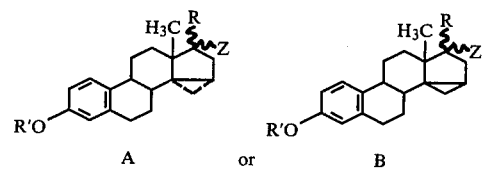

where R' is H or methyl;
R is a hydroxy, acetoxy, arylaminocarbonyloxy or alkylaminocarbonyloxy radical and
Z is H or a lower alkyl, or
R and Z together are oxygen.

2. A compound as defined in claim 1, which is 3-methoxy-14β,15β-methylene-estra-1,3,5(10)-triene-17β-ol.

3. A compound as defined in claim 1, which is 3-methoxy-14α,15α-methylene-estra-1,3,5(10)-triene-17α-ol.

4. A compound as defined in claim 1, which is 3-methoxy-14β,15β-methylene-estra-1,3,5(10)-triene-17α-ol.

5. A compound as defined in claim 1, which is 3-methoxy-14α,15α-methylene-estra-1,3,5(10)-triene-17β-ol.

6. A compound as defined in claim 1, which is 3-methoxy-17α-methyl-14β,15β-methylene-estra-1,3,5(10)-triene-17β-ol.

7. A compound as defined in claim 1, which is 3-methoxy-14β,15β-methylene-estra-1,3,5(10)-triene-17-one.

8. A compound as defined in claim 1, which is 3-methoxy-14α,15β-methylene-estra-1,3,5(10)-triene-17-one.

9. A compound as defined in claim 1, which is 17α-phenylaminocarbonyloxy-14β,15β-methylene-estra-1,3,5(10)-triene-3-methylether.

10. A compound as defined in claim 1, which is 17β-phenylaminocarbonyloxy-14β,15β-methylene-estra-1,3,5(10)-triene-3-methylether.

11. A compound as defined in claim 1, which is 17α-phenylaminocarbonyloxy-14β,15β-methylene-estra-1,3,5(10)-triene-3β-ol.

12. A process for the preparation of the compounds of claim 1, comprising: reacting Δ14,17α-or 17β-hydroxy compounds of the estrane series, which can include lower alkyls in the 17 position, with dihalogen methanes and a zinc-copper pair or with diazomethane and zinc iodide at room temperature up to 50° C. in organic solvents such as diethylether and mixtures of diethylether and ethylene glycol dimethylether, hydrocarbons, cyclic hydrocarbons and halogenated hydrocarbons as well as their mixtures with ethers, so as to obtain the 14α,15α-methylene-17α-hydroxy or 14β,15β-methylene-17β-hydroxy compounds of the estrane series; oxidizing the secondary 14,15-methylene-17-alcohols to 17-ketones by means of chromic oxide and aqueous sulfuric acid in acetone; reducing the resulting 14α,15α- or 14β,15β-methylene-17-ketones of the estrane series with complex metal hydrides to 14α,15α-methylene-17α-ols and 14β,15β-methylene-17β-ols as well as to their isomeric compounds, namely, the 14α,15α-methylene-17β-ols and 14β,15β-methylene-17α-ols, respectively; separating the components of the mixtures by chromatography; and converting above called compounds by means of acetic anhydride and pyridine into the corresponding 17α- and 17β-acetoxy-derivatives or by means of alkyl- or arylisocyanates directly or by means of phosogene via the corresponding chlorocarbonyloxy derivatives and successive reaction with amines into the 17α- and 17β-alkyl- or arylaminocarbonyloxy derivatives, if desired.

* * * * *